(12) United States Patent
Wolber et al.

(10) Patent No.: US 10,485,443 B2
(45) Date of Patent: Nov. 26, 2019

(54) ELECTRICAL INTERFACE SYSTEM

(71) Applicant: Halo Neuro, Inc., San Francisco, CA (US)

(72) Inventors: Patrick Wolber, San Francisco, CA (US); Tal Bar-Or, San Francisco, CA (US); Brett Wingeier, San Francisco, CA (US); Ian Shain, San Francisco, CA (US); Colin Davis, San Francisco, CA (US); Victoria Hammett, San Francisco, CA (US)

(73) Assignee: Halo Neuro, Inc., San Francisco, CA (US)

( * ) Notice: Subject to any disclaimer, the term of this patent is extended or adjusted under 35 U.S.C. 154(b) by 186 days.

(21) Appl. No.: 15/627,717

(22) Filed: Jun. 20, 2017

(65) Prior Publication Data

US 2017/0360321 A1  Dec. 21, 2017

Related U.S. Application Data

(60) Provisional application No. 62/352,387, filed on Jun. 20, 2016, provisional application No. 62/468,624, (Continued)

(51) Int. Cl.
*A61B 5/0478* (2006.01)
*A61B 5/0496* (2006.01)
(Continued)

(52) U.S. Cl.
CPC .......... *A61B 5/0478* (2013.01); *A61B 5/0492* (2013.01); *A61B 5/0496* (2013.01);
(Continued)

(58) Field of Classification Search
None
See application file for complete search history.

(56) References Cited

U.S. PATENT DOCUMENTS 3,472,233 A 10/1969 Sarbacher
4,928,696 A  5/1990 Henderson et al.
(Continued)

FOREIGN PATENT DOCUMENTS

CN 103517732 A 1/2014
EP 2449961 5/2012
(Continued)

OTHER PUBLICATIONS

Office Action for Chinese Patent Application No. 201710611160.3 dated Jul. 31, 2019.

*Primary Examiner* — Brian T Gedeon
(74) *Attorney, Agent, or Firm* — Jeffrey Schox; Caitlin Ploch

(57) ABSTRACT

A system for providing an electrical interface between a transducer and a transducer support device, the system comprising: a body mounted to the transducer support device, the body comprising an interface-to-transducer coupling region; a interface-to-electronics subsystem coupling region coupled to the body and contiguous with the interface-to-transducer coupling region, the system defining a fluid sealing region surrounding at least one of the interface-to-transducer and the interface-to-electronics subsystem coupling region; the system comprising an operation mode defining a sealed electrical pathway between the transducer and the transducer support device, wherein: the fluid sealing region is coupled to a complementary transducer sealing region, and the elastically deformable coupling region is biased against an electrical contact of the transducer with the fluid sealing region preventing fluid from reaching the electrical contact of the transducer.

22 Claims, 14 Drawing Sheets

Related U.S. Application Data filed on Mar. 8, 2017, provisional application No. 62/486,348, filed on Apr. 17, 2017.

(51) Int. Cl.
*A61B 5/0492* (2006.01)
*A61N 1/04* (2006.01)
*A61B 5/00* (2006.01)
*A61B 5/01* (2006.01)

(52) U.S. Cl.
CPC .......... *A61B 5/4836* (2013.01); *A61B 5/6801* (2013.01); *A61B 5/6814* (2013.01); *A61B 5/6831* (2013.01); *A61N 1/0456* (2013.01); *A61B 5/01* (2013.01); *A61B 5/6824* (2013.01); *A61B 2562/0204* (2013.01); *A61B 2562/0209* (2013.01); *A61B 2562/0217* (2017.08); *A61B 2562/0219* (2013.01); *A61B 2562/043* (2013.01)

(56) References Cited

U.S. PATENT DOCUMENTS

| | | |
|---|---|---|
| 4,977,895 A | 12/1990 | Tannenbaum |
| 5,058,605 A | 10/1991 | Slovak |
| 5,087,242 A | 2/1992 | Petelenz et al. |
| 5,137,817 A | 8/1992 | Busta et al. |
| 5,250,023 A | 10/1993 | Lee et al. |
| 5,387,231 A | 2/1995 | Sporer |
| 5,622,168 A | 4/1997 | Keusch et al. |
| 6,077,237 A | 6/2000 | Campbell et al. |
| 6,263,226 B1 | 7/2001 | Axelgaard et al. |
| 6,379,324 B1 | 4/2002 | Gartstein et al. |
| 6,480,743 B1 | 11/2002 | Kirkpatrick et al. |
| 6,505,079 B1 | 1/2003 | Foster et al. |
| 6,510,333 B1 | 1/2003 | Licata et al. |
| 7,024,247 B2 | 4/2006 | Gliner et al. |
| 7,551,952 B2 | 6/2009 | Gevins et al. |
| 7,610,095 B2 | 10/2009 | Naisberg |
| 7,813,802 B2 | 10/2010 | Tcheng et al. |
| 7,818,515 B1 | 10/2010 | Umbehocker et al. |
| 7,828,947 B2 | 11/2010 | Oki et al. |
| 7,877,146 B2 | 1/2011 | Rezai et al. |
| 7,894,905 B2 | 2/2011 | Pless et al. |
| 7,966,073 B2 | 6/2011 | Pless et al. |
| 7,988,917 B2 | 8/2011 | Roesicke et al. |
| 8,116,875 B2 | 2/2012 | Osypka et al. |
| 8,121,694 B2 | 2/2012 | Molnar et al. |
| 8,239,030 B1 | 8/2012 | Hagedorn et al. |
| 8,290,596 B2 | 10/2012 | Wei et al. |
| 8,301,265 B2 | 10/2012 | Starkebaum |
| 8,349,554 B2 | 1/2013 | Bahrami et al. |
| 8,380,316 B2 | 2/2013 | Hagedorn et al. |
| 8,419,716 B2 | 4/2013 | Weissenrieder-Norlin et al. |
| 8,473,063 B2 | 6/2013 | Gupta et al. |
| 8,554,324 B2 | 10/2013 | Brocke |
| 8,583,237 B2 | 11/2013 | Bedenbaugh |
| 8,591,392 B2 | 11/2013 | Bentwich et al. |
| 8,626,259 B2 | 1/2014 | Besio |
| 8,706,181 B2 | 4/2014 | Stypulkowski et al. |
| 8,795,174 B2 | 8/2014 | Manicka et al. |
| 8,818,515 B2 | 8/2014 | Bikson et al. |
| 8,838,247 B2 | 9/2014 | Hagedorn et al. |
| 8,874,220 B2 | 10/2014 | Draghici et al. |
| 8,874,227 B2 | 10/2014 | Simon et al. |
| 8,880,173 B2 | 11/2014 | Diubaldi et al. |
| 8,903,494 B2 | 12/2014 | Goldwasser et al. |
| 8,938,301 B2 | 1/2015 | Hagedorn |
| 8,979,837 B2 | 3/2015 | De La Rama et al. |
| 8,989,863 B2 | 3/2015 | Osorio |
| 9,002,458 B2 | 4/2015 | Pal et al. |
| 9,080,918 B2 | 7/2015 | Fishel et al. |
| 9,186,505 B2 | 11/2015 | Katsnelson |
| 9,393,430 B2 | 7/2016 | Demers et al. |
| 9,399,126 B2 | 7/2016 | Pal et al. |
| 9,433,774 B2 | 9/2016 | Dar et al. |
| 9,440,063 B2 | 9/2016 | Ho et al. |
| 9,440,070 B2 | 9/2016 | Goldwasser et al. |
| 9,486,618 B2 | 11/2016 | Wingeier et al. |
| 9,517,345 B2 | 12/2016 | Meffin et al. |
| 9,630,005 B2 | 4/2017 | Wingeier et al. |
| 9,643,001 B2 | 5/2017 | Wu et al. |
| 9,731,127 B2 | 8/2017 | Kealey et al. |
| 9,757,561 B2 | 9/2017 | Wingeier et al. |
| 9,770,204 B2 | 9/2017 | Wu et al. |
| 9,782,585 B2 | 10/2017 | Wingeier |
| 9,802,042 B2 | 10/2017 | Wingeier et al. |
| 9,889,290 B2 * | 2/2018 | Wingeier ............. A61B 5/0478 |
| 9,913,973 B2 | 3/2018 | Yanaki |
| 10,238,870 B2 | 3/2019 | Pilly et al. |
| 2002/0169485 A1 | 11/2002 | Pless et al. |
| 2004/0019370 A1 | 1/2004 | Gliner et al. |
| 2005/0165460 A1 | 7/2005 | Erfan |
| 2006/0229502 A1 | 10/2006 | Pollock et al. |
| 2006/0259094 A1 | 11/2006 | Grinshpoon et al. |
| 2007/0015984 A1 | 1/2007 | Yeo et al. |
| 2007/0038265 A1 | 2/2007 | Tcheng et al. |
| 2007/0118070 A1 | 5/2007 | Cormier et al. |
| 2007/0213783 A1 | 9/2007 | Pless |
| 2007/0237678 A1 | 10/2007 | Roesicke et al. |
| 2007/0237797 A1 | 10/2007 | Peyman |
| 2007/0238945 A1 | 10/2007 | Delic et al. |
| 2007/0250145 A1 | 10/2007 | Kraus et al. |
| 2008/0004676 A1 | 1/2008 | Osypka et al. |
| 2008/0021520 A1 | 1/2008 | Dietrich |
| 2008/0027345 A1 | 1/2008 | Kumada et al. |
| 2009/0069803 A1 | 3/2009 | Starkebaum |
| 2009/0187159 A1 | 7/2009 | Greger et al. |
| 2010/0030129 A1 | 2/2010 | Nitzan et al. |
| 2010/0213070 A1 | 8/2010 | Oki et al. |
| 2010/0268287 A1 | 10/2010 | Celnik |
| 2011/0054288 A1 | 3/2011 | Besio |
| 2011/0112590 A1 | 5/2011 | Wu et al. |
| 2011/0118806 A1 | 5/2011 | Pascual-Leone et al. |
| 2012/0184894 A1 | 7/2012 | Imran et al. |
| 2012/0271377 A1 | 10/2012 | Hagedorn et al. |
| 2012/0289869 A1 | 11/2012 | Tyler |
| 2013/0085347 A1 | 4/2013 | Manicka et al. |
| 2013/0113059 A1 | 5/2013 | Song et al. |
| 2013/0184779 A1 | 7/2013 | Bikson et al. |
| 2013/0204315 A1 | 8/2013 | Wongsarnpigoon et al. |
| 2013/0261706 A1 | 10/2013 | Mirro et al. |
| 2014/0316505 A1 | 10/2014 | Yanaki |
| 2015/0005841 A1 | 1/2015 | Pal et al. |
| 2015/0065838 A1 | 3/2015 | Wingeier et al. |
| 2015/0066104 A1 | 3/2015 | Wingeier et al. |
| 2015/0088224 A1 | 3/2015 | Goldwasser et al. |
| 2015/0238759 A1 | 8/2015 | Katsnelson |
| 2015/0238762 A1 | 8/2015 | Pal et al. |
| 2015/0328467 A1 | 11/2015 | Demers et al. |
| 2015/0335877 A1 | 11/2015 | Jeffery et al. |
| 2015/0352357 A1 | 12/2015 | Wei et al. |
| 2015/0360027 A1 | 12/2015 | Bachinski et al. |
| 2016/0022981 A1 | 1/2016 | Wingeier et al. |
| 2016/0175589 A1 | 6/2016 | Wingeier |
| 2016/0184585 A1 | 6/2016 | Kealey et al. |
| 2016/0256105 A1 | 9/2016 | Boyle et al. |
| 2016/0303362 A1 | 10/2016 | Wu et al. |
| 2016/0346530 A1 | 12/2016 | Jeffery et al. |
| 2016/0361541 A1 | 12/2016 | Wingeier et al. |
| 2017/0021158 A1 | 1/2017 | Wingeier et al. |
| 2017/0224978 A1 | 8/2017 | Lee |
| 2017/0224990 A1 | 8/2017 | Goldwasser et al. |
| 2017/0361096 A1 | 12/2017 | Wingeier |
| 2017/0368344 A1 | 12/2017 | Ironi et al. |
| 2018/0021565 A1 | 1/2018 | Dar et al. |

FOREIGN PATENT DOCUMENTS

| | | |
|---|---|---|
| EP | 2449961 A1 | 5/2012 |
| JP | 2010152731 A | 7/2010 |
| KR | 101685124 | 12/2009 |
| KR | 20150088224 A | 7/2015 |

(56) References Cited

FOREIGN PATENT DOCUMENTS

| KR | 20170021158 A | 2/2017 |
|----|---------------|--------|
| KR | 20170028197 A | 3/2017 |
| KR | 20180021565 A | 3/2018 |
| WO | 2008048471 A2 | 4/2008 |
| WO | 134763 | 11/2009 |
| WO | 2013004763 A1 | 1/2013 |
| WO | 113059 | 8/2013 |

\* cited by examiner

ELECTRICAL INTERFACE SYSTEM

CROSS-REFERENCE TO RELATED APPLICATIONS

This application is related to U.S. application Ser. No. 15/250,070 filed 29 Aug. 2016, U.S. application Ser. No. 15/355,499 filed 18 Nov. 2016, and U.S. application Ser. No. 15/335,240 filed 26 Oct. 2016, which are each incorporated in its entirety herein by this reference.

This application also claims the benefit of U.S. Provisional Application Ser. No. 62/352,387 filed 20 Jun. 2016, U.S. Provisional Application Ser. No. 62/468,624 filed 8 Mar. 2017, and U.S. Provisional Application Ser. No. 62/486,348 filed 17 Apr. 2017, which are each incorporated in its entirety herein by this reference.

TECHNICAL FIELD

This invention relates generally to the bioelectrical device field, and more specifically to a new and useful electrical interface system in the bioelectrical device field.

BACKGROUND

Transducer interface systems are used to sense inputs from a contextual environment and/or provide outputs to a contextual environment (e.g., a user, an environment surrounding a user). In a specific application, such an interface system can include an electrode that provides stimulation to a body region of the user, and/or an electrode that senses signals from the body region of the user (e.g., electrical potentials from the brain or scalp). In consideration of modularity, it is sometimes desirable to design such transducer interface systems in a manner that facilitates easy interchange of transducer units (e.g., to provide different functions), facilitates easy attachment and/or removal of transducer units (e.g., for storage), or facilitates easy replacement of worn or damage transducer units (e.g., to allow replacement of contaminated electrodes).

Coupling regions between transducers and their support devices are often prone to corrosion and other forms of degradation, especially if such transducers are used in environments that enhance corrosion (e.g., saline/electrolyte environments, environments that promote crevice corrosion, environments that promote galvanic corrosion, etc.). Current systems, however, fail to adequately prevent corrosion of contact regions between transducers and their support devices, fail to achieve corrosion prevention (or other forms of damage prevention) in a low-cost manner, fail to achieve damage prevention in a space-efficient manner, and/or fail to achieve damage prevention in a manner that accounts for user considerations. Furthermore, in the context of electrodes, current systems fail to prevent undesired bridging between multiple contacts of the same or different electrodes, which can substantially damage the electrical contacts involved and/or divert stimulation current through an undesired path. Even further, in applications that involve persistent voltage differentials between electrode contacts, and/or stimulation using waveforms other than charge-balanced biphasic pulses (e.g., transcranial direct current stimulation), traditional techniques for protecting electrode contacts, such as some plating techniques, are often insufficient in preventing corrosion.

Thus, there is a need in the bioelectrical device field for a new and useful electrical interface system. This invention provides such a new and useful system.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System

Figure 1A:
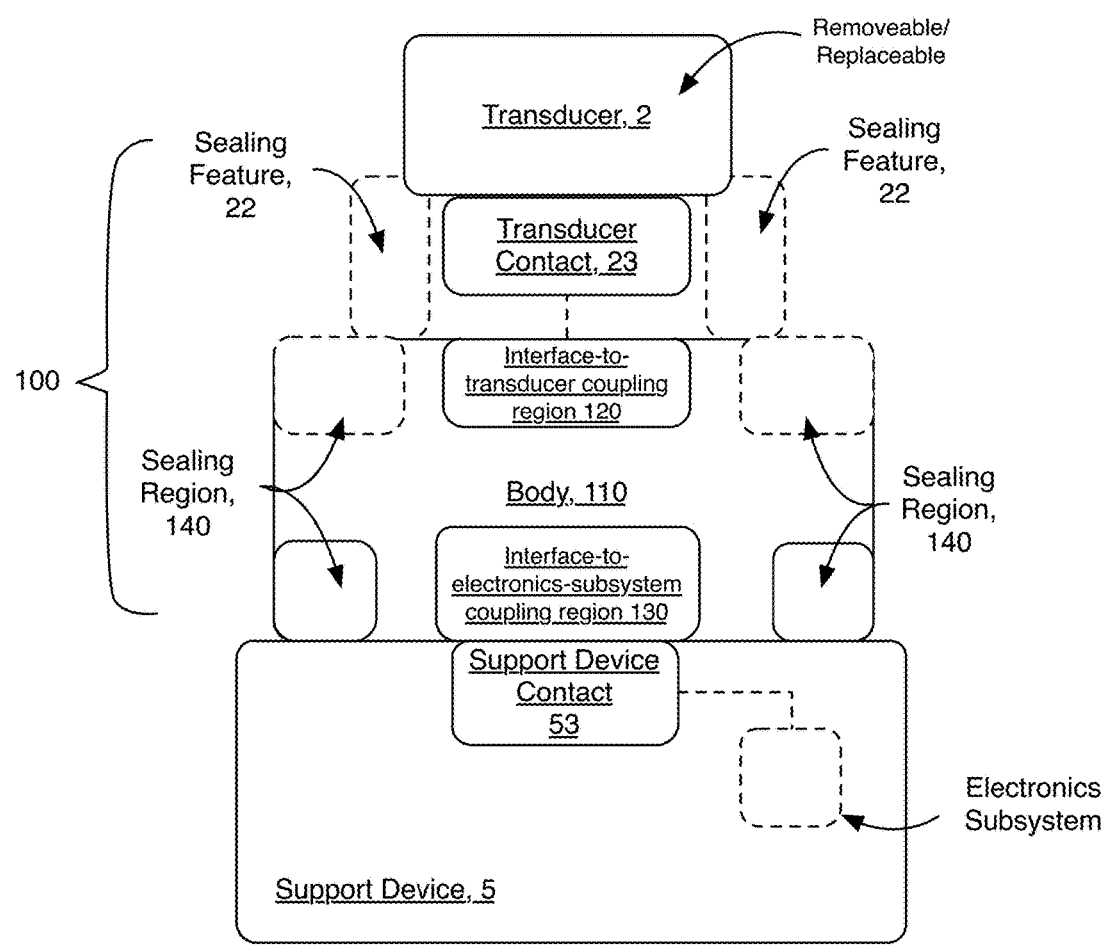
FIGS. 1A and 1B depict schematics of embodiments of an electrical interface system.

As shown in FIG. 1A, an embodiment of a system 100 for providing an electrical interface between a transducer 2 and a transducer support device 5 includes a body 110 mounted to the transducer support device 5, the body 110 comprising, contiguous with, or otherwise coupled to (e.g., in communication with): an interface-to-transducer electrical coupling region 120; an interface-to-electrical-subsystem coupling region 130 in electrical communication with (e.g., joined to by a continuous path of electrically conductive material) the interface-to-transducer electrical coupling region 120; and a fluid sealing region 140 coupled to the transducer support device 5 and surrounding the interface-to-electrical-subsystem coupling region 130 and support device contact 53. In this embodiment, the system 100 can include an operation mode (not shown) defining a sealed electrical pathway between the transducer 2 and the transducer support device 5, wherein: the fluid sealing region 140 is coupled to a complementary transducer sealing region 22, and the interface-to-transducer electrical coupling region 120 is biased against an electrical contact 23 of the transducer 2 with the fluid sealing region 140 preventing fluid from reaching the electrical contact 23 of the transducer 2.

Figure 1B:
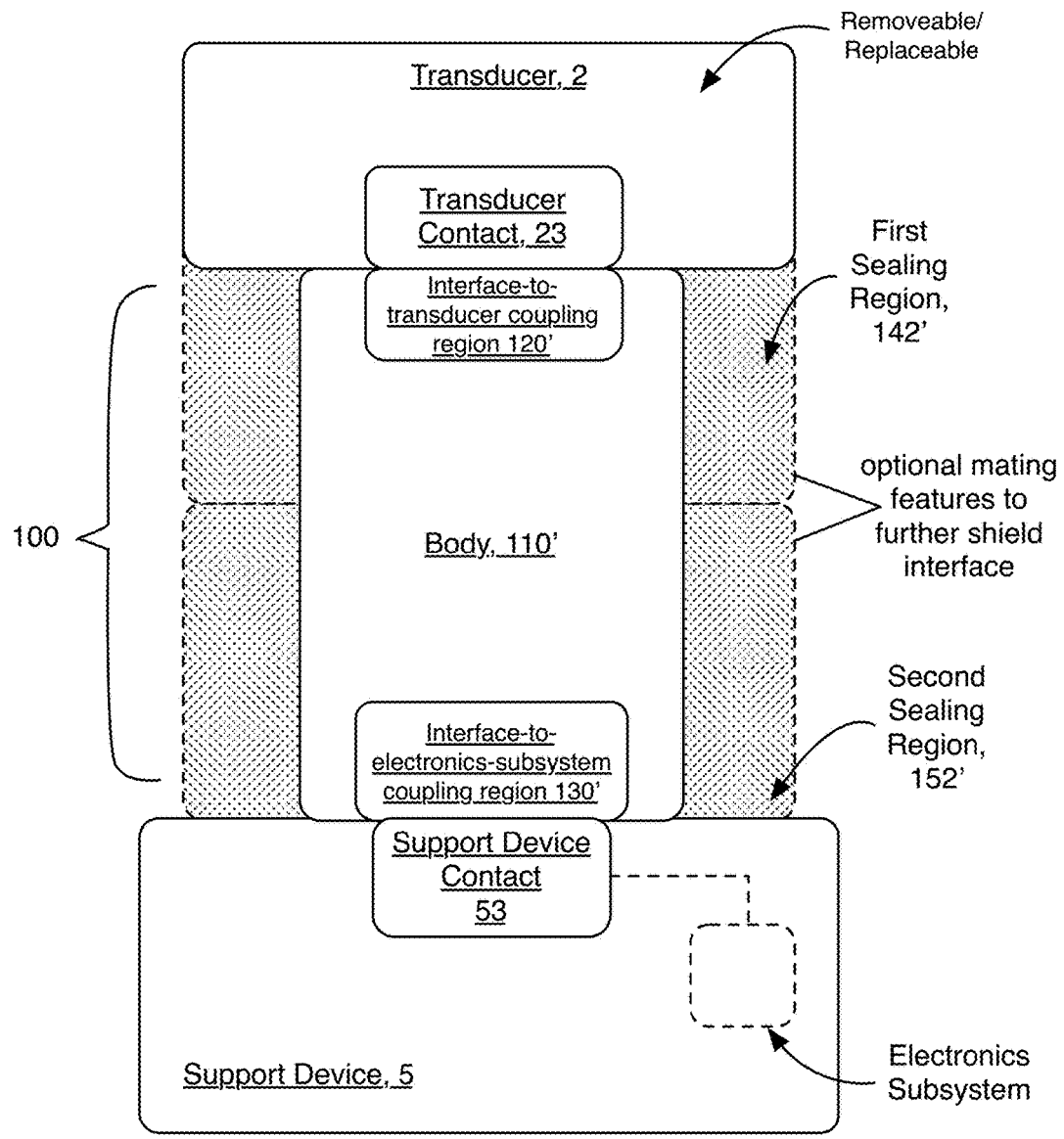

In another embodiment, as shown in FIG. 1B, a system for providing an electrical interface between a transducer 2 and a transducer support device 5 can include a body 110' mounted to the support device 5, the body 110' comprising, contiguous with, or otherwise coupled to (e.g., in communication with): an interface-to-transducer coupling region 120'; an interface-to-electronics-subsystem coupling region 130' in electrical communication with (e.g., joined to by a continuous path of electrically conductive material) the interface-to-transducer electrical coupling region 120'; a first sealing region 142' coupled to a complementary transducer sealing region 22' and surrounding the interface-to-transducer coupling region 120' and transducer contact 23; and a second sealing region 152' coupled to the support device 5 and surrounding the interface-to-electronics-subsystem coupling region 130' and support device contact 53. The system can further comprise an operation mode defining a fully sealed electrical pathway between the transducer and the support device, wherein the first fluid sealing region 142' and second fluid sealing region 152' are contiguous or coupled to prevent fluid ingress or contact with electrically conductive portions of the system, and the first fluid sealing region 142' and the second fluid sealing region 152' are electrical insulators.

The system 100 functions to provide a robust and reliable interface between a transducer and a transducer support device, in a manner that facilitates easy interchange of transducer units (e.g., to provide different functions), facilitates easy attachment and/or removal of transducer units (e.g., for storage), or facilitates easy replacement of worn or damage transducer units (e.g., to allow replacement of contaminated electrodes). Furthermore, the system 100 functions to provide a corrosion-proof (or substantially corrosion-resistant) interface between transducers and their support devices, especially in use cases that would otherwise promote active and/or passive corrosion of electrical interfaces (e.g., saline/electrolyte environments, environments that promote crevice corrosion, environments that promote galvanic corrosion, etc.). The system 100 can thus mitigate corrosion and also seal associated metallic conductors from ingress of fluids that would otherwise enhance corrosion. In particular, the system 100 can provide a mechanism that prevents undesired bridging between multiple contacts of a single electrode or multiple electrodes of a stimulation system, thereby preventing damage to the electrical contacts involved. Embodiments of the system 100 can even operate robustly in applications that involve persistent voltage differentials between electrode contacts, and/or stimulation using waveforms other than charge-balanced biphasic pulses (e.g., transcranial direct current stimulation) in comparison to some techniques such as plating, which are often insufficient in preventing or reducing corrosion. In particular, the system 100 can also provide a mechanism that allows and/or tolerates bridging between multiple contacts of a single electrode or multiple electrodes of a stimulation system in the case of presence or ingress of electrolyte fluid into the system, but minimizes or in some cases prevents corrosion and/or damage due to corrosion (e.g. by ensuring that the only electrically active surfaces that are exposed to electrolyte are formed of a material that minimizes corrosion or damage due to corrosion, such as carbon-bearing silicone rubber. In some embodiments of the system 100, the undesirability, economic, and/or cosmetic impact of corrosion damage is minimized because the portions of the system 100 that are built into the support device 5 and/or are difficult or expensive to replace, such as an electrical contact of the electronic subsystem, are protected from exposure to corrosion promoting agents (e.g., electrolyte) while portions of the system that are easy to replace (such as electrical contact 23 mounted on replaceable transducer 2) are less protected from exposure to corrosion promoting agents (e.g., electrolyte).

Variations of the system 100 are configured for stimulation devices situated outside the body of a user, such as stimulation devices delivering transcranial electrical stimulation, wherein the stimulation devices are designed for wearability (e.g., in a manner that reduces bulkiness). As such, in contrast to other implanted devices (e.g., pacemakers, etc.), the system 100 can be designed in a manner that is streamlined for wearability and does not require a level of robustness (e.g., corrosion resistance over a lifetime of implanted use) associated with implanted medical devices.

In some applications, the system 100 can provide an electrical interface between transducers/electrodes and an electronic device that supports and positions the transducers/electrodes at a body region of a user. In a specific application, the system 100 can provide an electrical interface between electrodes for electrical stimulation (e.g., such as the electrodes described in U.S. application Ser. No. 14/470,683 titled "Electrode System for Electrical Stimulation" and filed on 27 Aug. 2014, U.S. application Ser. No. 14/878,647 titled "Electrode System for Electrical Stimulation" and filed on 8 Oct. 2015, and U.S. application Ser. No. 15/426,212 titled "Method and System for Improving Provision of Electrical Stimulation" and filed on 7 Feb. 2017, which are each incorporated in their entireties by this reference) and an electrode support device (e.g., such as the support devices described in U.S. application Ser. No. 15/335,240 titled "Electrode Positioning System and Method" and filed on 26 Oct. 2016, which is herein incorporated in its entirety by this reference). Additionally or alternatively, the system 100 can support or otherwise facilitate methods described in one or more of U.S. application Ser. No. 14/470,747 titled "Method and System for Providing Electrical Stimulation to a User" and filed on 27 Aug. 2014 and U.S. application Ser. No. 15/059,095 titled "Method and System for Providing Electrical Stimulation to a User" and filed on 2 Mar. 2016, which are each incorporated in their entireties herein by this reference.

The system 100 can additionally or alternatively support or interface any other transducers (e.g., optical sensors, optical emitters, ultrasonic transducers, etc.), additional sensors (e.g., temperature sensors, activity detecting sensors, sensors associated with position, velocity, or acceleration detection, biometric sensors, etc.) for sensing signals from the user, additional sensors (e.g., temperature sensors, barometric pressure sensors, light sensors, microphones, etc.) for sensing signals from the environment of the user, and any other suitable device in a robust manner. Similarly, the system 100 can additionally or alternatively be used to provide a corrosion-resistant and/or leakage-current-resistant electrical interface with any other suitable support device (e.g., non-wearable device, wrist-borne wearable device, limb-coupled wearable device, wearable device not coupled to a head region of a user, non-wearable device where robustness and compact form factor are desirable, etc.)

In embodiments of the system 100, regions of the body 110 such as the interface-to-transducer coupling region 120, the interface-to-electronics-subsystem coupling region 130, and the sealing region 140 can be multiple surfaces or couple at multiple points with other surfaces; for instance, the sealing region 140 can comprise a surface that couples with the support device 5 forming a first part of a gasket-like seal, and a second surface that couples with the support device at a different position or different set of points to form a second part of a gasket-like seal, wherein the first part and second part of the gasket-like seal operate together or redundantly to prevent or minimize electrolyte ingress. In another example, the interface-to-transducer coupling region 120 can comprise a surface that couples with the transducer contact 23 at a first contact area, and a second surface that couples with the transducer contact at a second contact area, wherein the first and second contact areas provide increased electrical contact or redundant electrical contact.

1.1 System—Body

As described above, the body 110 can be coupled to the transducer support device 5, and functions to provide, along with other elements of the system, electrical conductivity and sealing functions in a manner that mitigates corrosion of metallic contacts (e.g., of transducer elements, of electrode elements, of a support device, etc.). Various surfaces and/or regions of the body 110 can mate with surfaces of the transducer support device 5 and any transducers 2. The body no can thus function as a substrate to which other functional elements of the system 100 are coupled, as described in further detail below.

The body 110 is preferably composed of a material that is relatively stable in an environment with electrolytic reactions. In one variation, the body no includes carbon (e.g., graphite), which is electrically conductive and exhibits stability in the presence of electrolytic reactions (e.g., exhibits only gradual loss of structure in the form of elemental carbon when used as the anode of an electrolytic cell), and is resistant to passive corrosion. The body no, can however, additionally or alternatively include any other suitable molecular form of carbon, any other suitable non-metallic conductive materials (e.g., silicon, germanium) in any form, and/or any other suitable metallic conductive material.

The body 110 can additionally or alternatively include a matrix of material supporting conductive components. In one variation, the matrix can be composed of a polymer material, in order to provide sealing properties (e.g., in relation to prevention of fluid penetration past regions of the system) and properties associated with corrosion resistance. In embodiments in which the conductive component is carbon (e.g. carbon black), the matrix may act to hold carbon particles in place and prevent or retard the loss of structure which might otherwise occur (e.g., when carbon is used as the anode of an electrolytic cell). In specific examples, the matrix can be composed of silicone rubber. However, in other variations, the matrix can additionally or alternatively be composed of any other suitable polymeric or non-polymeric material.

In variations of the body 110 including a conductive component and a support matrix, the conductive component can be distributed throughout the support matrix (e.g., with a uniform distribution, with a non-uniform distribution), in order to provide electrical conductivity through the body 110. Alternatively, the conductive component can be patterned onto and/or within the support matrix, thereby defining electrically conductive pathways throughout the body no. However, the body no can additionally or alternatively be configured in any other suitable manner in relation to conductive components and support matrix components.

In relation to mechanical properties, the body 110 is preferably flexible, but can alternatively include rigid regions (e.g., in order to provide regions of intentional rigidity and/or deformation). In flexible variations, the body no can be elastically deformable during normal use, or can alternatively be plastically deformable during normal use. The body no can, however, have any other suitable mechanical properties (e.g., in relation to elasticity, in relation to hardness, in relation to stiffness, in relation to compressibility, in relation to density, in relation to porosity, in relation to strength, in relation to any other suitable mechanical properties). The body 100 is preferably impermeable to water and/or other polar fluids, and can exhibit a low level of wettability (e.g., in terms of contact angle). As such, the body no can be composed of a hydrophobic material. The body 110 can additionally or alternatively have any other suitable characteristics (e.g., in terms of hydrophilicity, in terms of hydrophobicity), any other suitable thermal properties, any other suitable electrical properties, any other suitable optical properties, and/or any other suitable material properties.

In a specific example, the body 110 can be composed of an elastomeric material (e.g., molded silicone rubber elastomer) containing or otherwise doped with a conductive component (e.g., carbon black particles). As such, the specific example of the body 110 can function to provide stability in relation to electrochemical reaction products that would otherwise result with use of other materials (e.g., metal) in electrolytic environments associated with electrical stimulation. Furthermore, such a composition can be readily configured to conform with metallic contacts to complete electrical pathways, while sealing off access to the metallic contacts, as described in more detail below. Thus, elastic properties of this material composition can facilitate a press-fit, snap-fit, or other interface against metal (or other conductive components) to ensure reliable contact. Furthermore, such a composition can ensure good conductivity, and in cases where conductivity is less than that of a traditional metallic contact (e.g., the conductivity achieved in embodiments of the present invention when using a conductive rubber material with volume resistivity of ~1 to 100 Ohm-cm), such a composition can still provide a desired amount of current flow and the resulting resistance to current flow can be materially less than the resistance presented by the transducer 23 and/or its connection to a target region such as the human scalp. As well, use of an imperfectly conducting substance such as carbon rubber can ensure a desirable distribution of current across multiple transducers. In more detail, in a system with multiple transducers, if the path to each transducer or electrode involved has some resistance (e.g., a low but non-trivial amount of resistance in comparison to the tissue resistance), it is more likely that all such endpoints will receive approximately similar amounts of current even in the presence of differences between the electrode-to-tissue resistance across each electrode or transducer. In the specific example, the carbon-bearing silicone rubber has a volume resistivity of 10-Ohm-cm and a Shore A hardness of 70. However, variations of the specific example can comprise a material having any other suitable volume resistivity (e.g., from 1-1000 Ohm-cm, any other suitable resistivity) and/or hardness (e.g., Shore A hardness from 20-90, any other suitable hardness).

In a version of this specific example, the body 110 and/or its regions that require electrical conductivity (e.g., interface-to-transducer coupling region 120 and/or interface-to-electronics-subsystem coupling region 130) can be created or extended by use of conductive adhesives or gasketing compounds such as carbon-conductive room-temperature vulcanizing silicone rubber (also known as carbon-conductive RTV) or similar materials. For instance, increased conductivity and adhesion between interface-to-electronics-subsystem coupling region 130 and the support device contact 53 can be created during manufacturing of support device 5 by depositing conductive RTV between the interface-to-electronics-subsystem coupling region 130 and the support device contact 53 and allowing it to cure such that the RTV adhesive becomes part of region 130. Also for instance, increased sealing ability between sealing region 140 and the support device 5 may be created during manufacturing of support device 5 by depositing non-conductive RTV between sealing region 140 and support device 5 and allowing it to cure such that the RTV adhesive becomes part of sealing region 140.

Furthermore, any other suitable material (e.g., metallic conductor, rubber doped with metal, etc.) can be used in the body no. For instance, in some variations involving lower current levels, the body 110 can be composed of another conductive polymer composition (e.g., polypyrrole, non-conductive polymer with a distribution of conductive components, etc.).

The body 110 preferably has a morphology that is complementary to corresponding regions of the transducer support device 5 and/or any transducers 2 or electrodes involved. As such, various surfaces of the body no can mate with surfaces of the transducer support device 5 and any transducers 2. In an example shown in FIGS. 2A and 2B, the body no can provide a substantially planar rear surface mounted to a portion of the support device 5, and have a suitable thickness that supports other portions of the system 100, as described in further detail below. Protrusions, recesses, ridges, troughs, regions of concavity, regions of convexity, and any other suitable morphological features associated with functions of the system 100 are described in further detail below.

Furthermore, the body no and other elements of the system 100 associated with the body 110 can be fabricated using a molding process (e.g., single shot molding, multi-shot molding, etc.), using a casting process, using an etching process, using a lithographic process, using a machining process, using a printing process, using a thermal process, or using any other suitable process.

1.2 Interface-to-Transducer Coupling Region

As described above, the body 110 includes an interface-to-transducer electrical coupling region 120, which functions to make elastic contact with a metallic contact on a transducer 2 (e.g., electrode) that is reversibly coupleable to (e.g., may be attached to and removed from) the support device 5. The interface-to-transducer electrical coupling region 120 can operate in an undeformed configuration prior to coupling with a corresponding conductive region (e.g., metallic contact) of a transducer 2 or electrode, and can operate in a deformed configuration upon coupling with a corresponding conductive region (e.g., metallic contact) of a transducer 2 or electrode, thereby ensuring and maintaining contact with the transducer 2 or electrode during use. As such, coupling between the interface-to-transducer electrical coupling region 120 and a corresponding conductive region (e.g., metallic contact) of a transducer 2 or electrode preferably produces a biasing force between the elastically deformable coupling region and at least some portion of the corresponding conductive region 23 of a transducer 2 or electrode. In more detail, implementing materials that elastically deform, in at least one of the interface-to-transducer electrical coupling region 120 and a corresponding conductive region of the transducer 2, can provide proper and reliable electrical contact between two similar or dissimilar contacts (e.g., a carbon-rubber contact and a metallic contact), by providing greater contact area between the two contacts. In some embodiments, the conductive contact 23 of a transducer 2 or electrode may be metallic or substantially metallic; in other embodiments, the conductive contact 23 may comprise non-metallic materials, such as carbon-bearing silicone rubber.

The interface-to-transducer electrical coupling region 120 preferably has the same material composition as the body 110, as described above; however, the interface-to-transducer electrical coupling region 120 can alternatively have any other suitable material composition in relation to material properties associated with electrical conductivity and elastic deformation behavior. The interface-to-transducer electrical coupling region 120 is preferably of unitary construction with the material of the body 110 (e.g., in relation to a single molding process); however, the interface-to-transducer electrical coupling region 120 can alternatively be physically coextensive with the body 110. Still alternatively, the interface-to-transducer electrical coupling region 120 can be formed separately from the body 110, but otherwise coupled to the base in any other suitable manner (e.g., with a thermal bonding process, with an electrically conductive adhesive layer, etc.).

Figure 3:
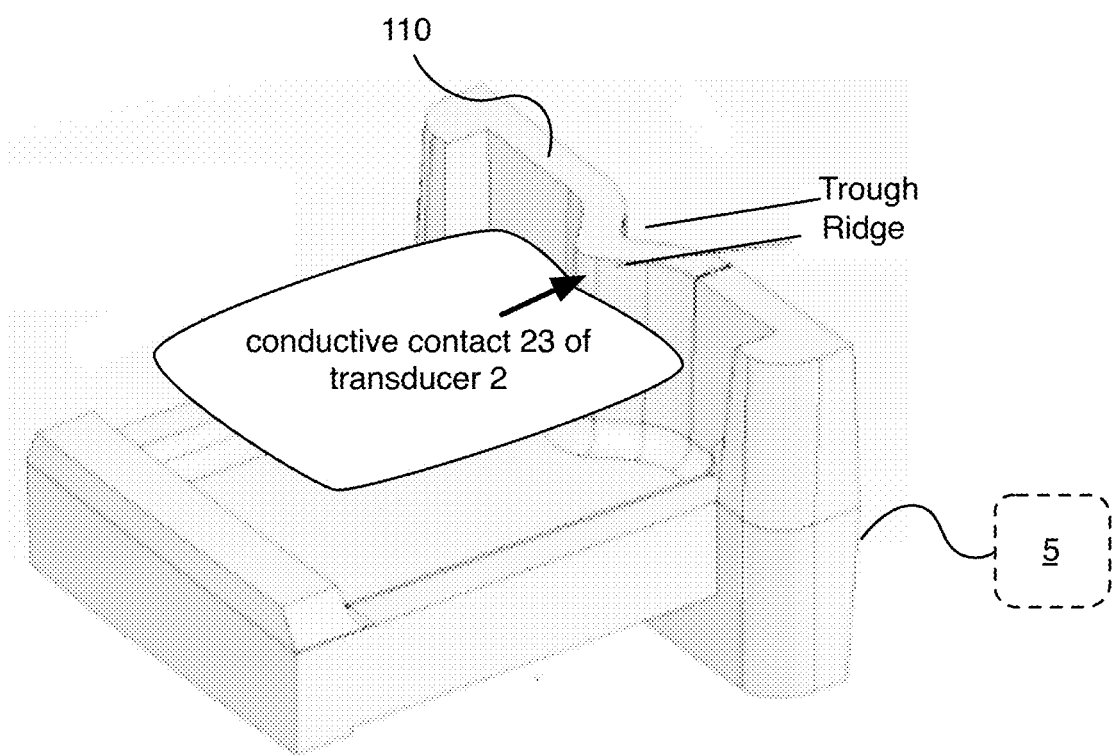
FIG. 3 depicts a schematic of an example of an embodiment of an electrical interface system.

The interface-to-transducer electrical coupling region 120 preferably comprises a protrusion of material coupled to the body 110, wherein, in operation modes of the system 100, the protrusion interfaces with a contact on a transducer 2 (e.g., electrode) that is reversibly coupleable to the support device 5. In one variation, the protrusion includes a ridge of material extending from the body 110 in a manner that allows the interface-to-transducer electrical coupling region 120 to couple to a corresponding contact 23. In a specific example of this variation, as shown in FIG. 3, the ridge of material protrudes away from the rear surface of the body 110' along the height of the body 110, wherein the rear surface of the body 110 has an elongated recess (e.g., trough) immediately opposite the ridge of material in order to further allow the ridge to deform elastically upon making contact with a contact 23 of a corresponding transducer 2 or electrode as the contact 23 moves substantially in the direction shown by the arrow in FIG. 3.

In other variations, the interface-to-transducer electrical coupling region 120 can comprise any other suitable form of protrusion (e.g., protruding region, convex surface, etc.), an array of protrusions (e.g., array of protruding regions, array of convex surfaces, etc.), any suitable form of recess (e.g., recessed region, concave surface, etc.) and/or an array of recesses. Protrusions/recesses can have polygonal cross sections, circular cross sections, semi-circular cross sections, ellipsoidal cross sections, hemi-ellipsoidal cross sections, amorphous cross sections, and/or any other suitable cross section defined along any axis of the protrusion/recess. Similarly, in relation to arrays, arrays of protrusions/recesses can be rectangular, circular, ellipsoidal, or any other suitable type of array.

Figure 4A:
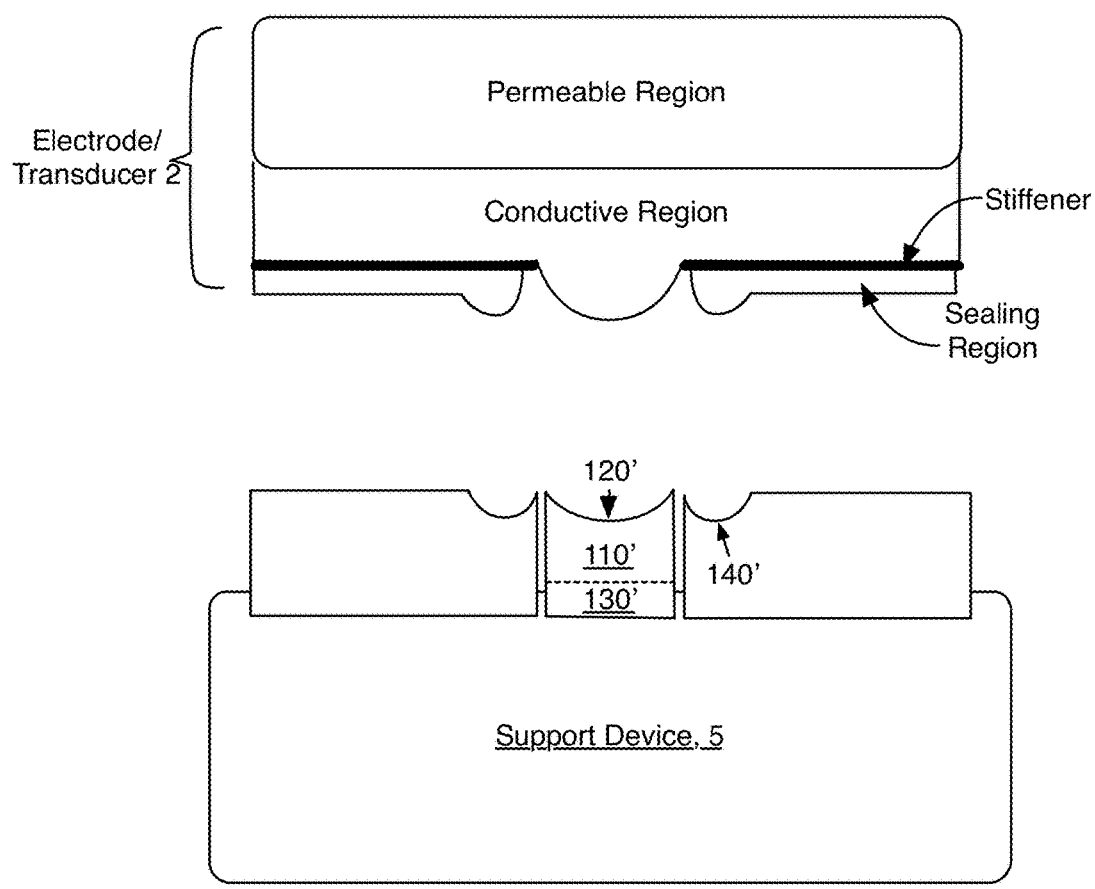
FIGS. 4A and 4B depict schematics of a variation of an embodiment of an electrical interface system.
Figure 4B:
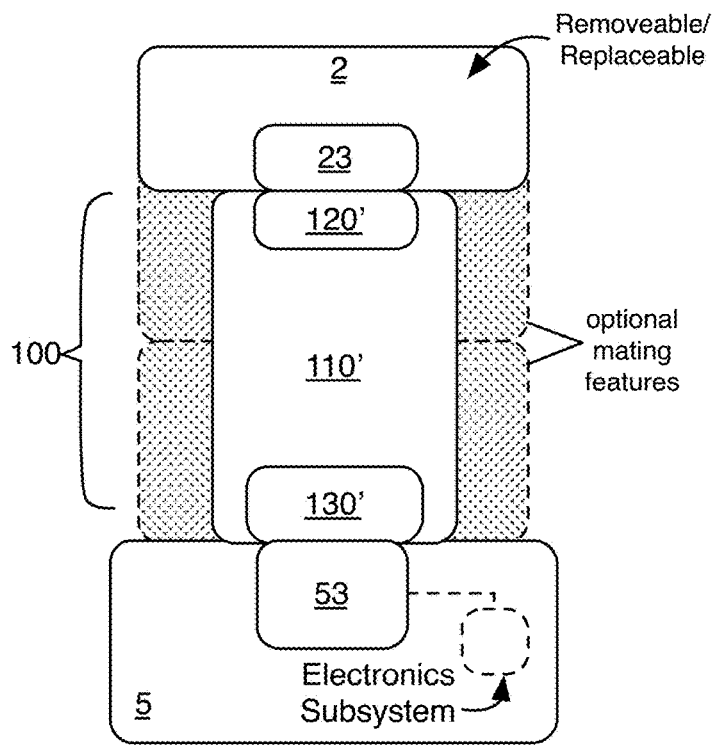
Figure 4B:
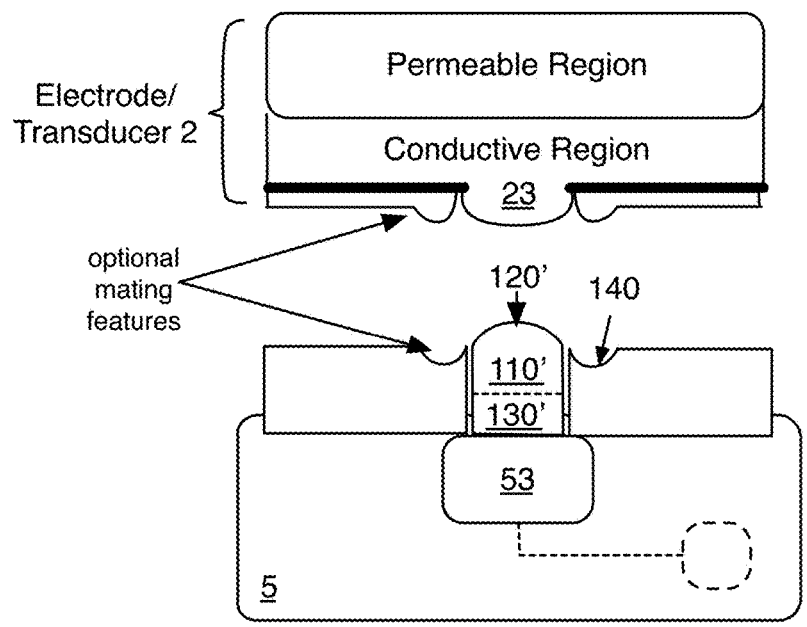

In an alternative example of the interface-to-transducer electrical coupling region 120', as shown in FIGS. 4A and 4B, the interface-to-transducer electrical coupling region 120', with the interface-to-electrical-subsystem coupling region 130', comprises a concave surface (e.g., circular recess) physically coextensive with a base region mounted to a support device 5, wherein the concave surface is compliant and mates with a protruding region of a transducer 2 or electrode. However, variations of the alternative example can be configured in any other suitable manner, for instance where the interface-to-transducer electrical coupling region 120' presents a convex surface to the transducer contact 23' wherein the convex surface is compliant.

Furthermore, while the interface-to-transducer electrical coupling region 120 is described above as being positioned approximately centrally and spanning a width of the body 110, the interface-to-transducer electrical coupling region 120 can alternatively have any other suitable position in relation to alignment with conductive contacts on a corresponding transducer 2 or electrode that is supported by the support device 5. As such, the interface-to-transducer electrical coupling region 120 can be located centrally with another orientation (e.g., spanning a height dimension of the body 110), peripherally located (e.g., along any edge of the body 110), or positioned in any other suitable manner relative to the body 110.

1.3 Interface-to-Electrical-Subsystem Coupling Region

As shown in FIGS. 1A and 1B, the system 100 comprises an interface-to-electrical-subsystem coupling region 130 coupled to the body 110 and contiguous, physically coextensive, or in electrical communication with (e.g., joined to by a continuous path of electrically conductive material) the interface-to-transducer electrical coupling region 120, wherein the interface-to-electrical-subsystem coupling region 130 functions to make electrical contact with a pad (e.g., a metallic pad) of an electronics subsystem associated with at least one of the transducer 2 and the support device 5 (described in further detail below). The interface-to-electrical-subsystem coupling region 130 also cooperates with the body 110 to define a fluid sealing region 140 surrounding the interface-to-electrical-subsystem coupling region 130, which seals portions of the interface-to-electrical-subsystem coupling region 130 and support device contact 53 against ingress and prevents fluid (e.g., electrolyte fluid) from reaching corrosion-prone components of the electrical interface between the transducer 2 or electrode and the support device 5.

The interface-to-electrical-subsystem coupling region 130 preferably has the same material composition as the body 110, as described above; however, the interface-to-electrical-subsystem coupling region 130 can alternatively have any other suitable material composition in relation to material properties associated with electrical conductivity and elastic deformation behavior. The interface-to-electrical-subsystem coupling region 130 is preferably of unitary construction with the material of the body 110 (e.g., in relation to a single molding process); however, the interface-to-electrical-subsystem coupling region 130 can alternatively be physically coextensive with the body 110. Still alternatively, the interface-to-electrical-subsystem coupling region 130 can be formed separately from the body 110, but otherwise coupled to the base in any other suitable manner (e.g., with a thermal bonding process, with an electrically conductive adhesive layer, etc.).

Figure 2A:
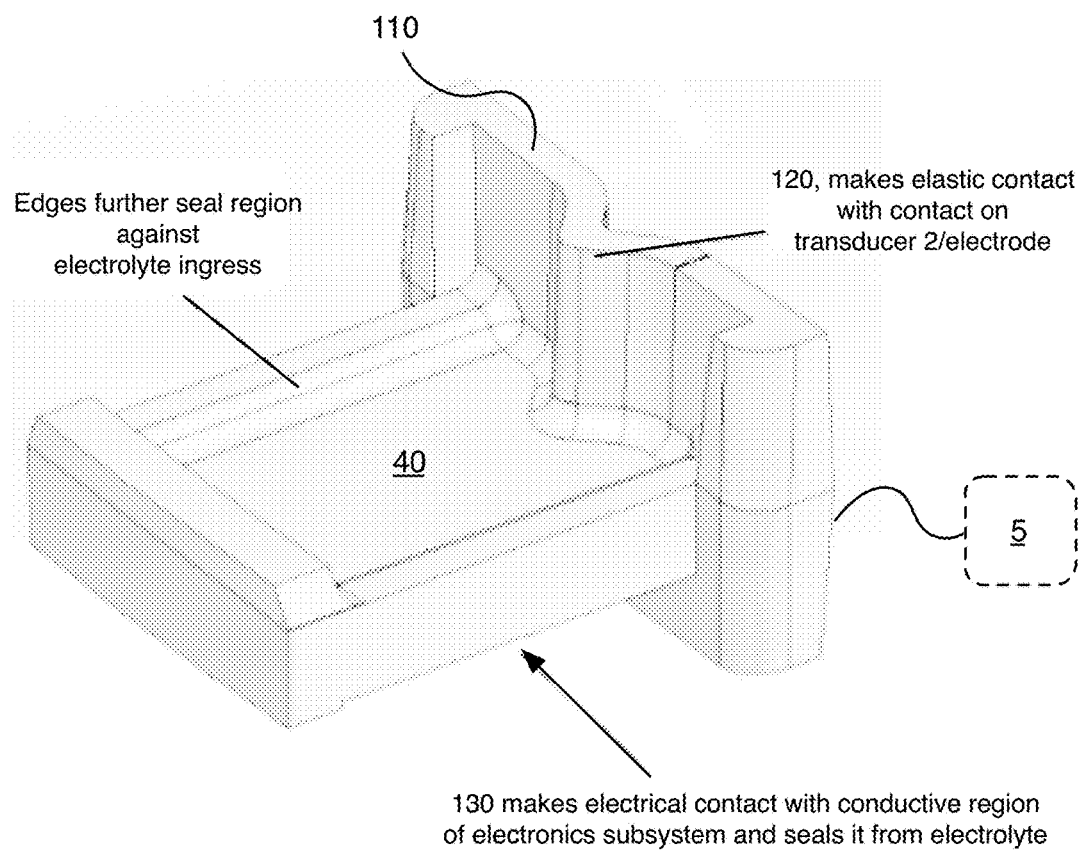
FIGS. 2A and 2B depict schematics of an example of an embodiment of an electrical interface system.
Figure 2B:
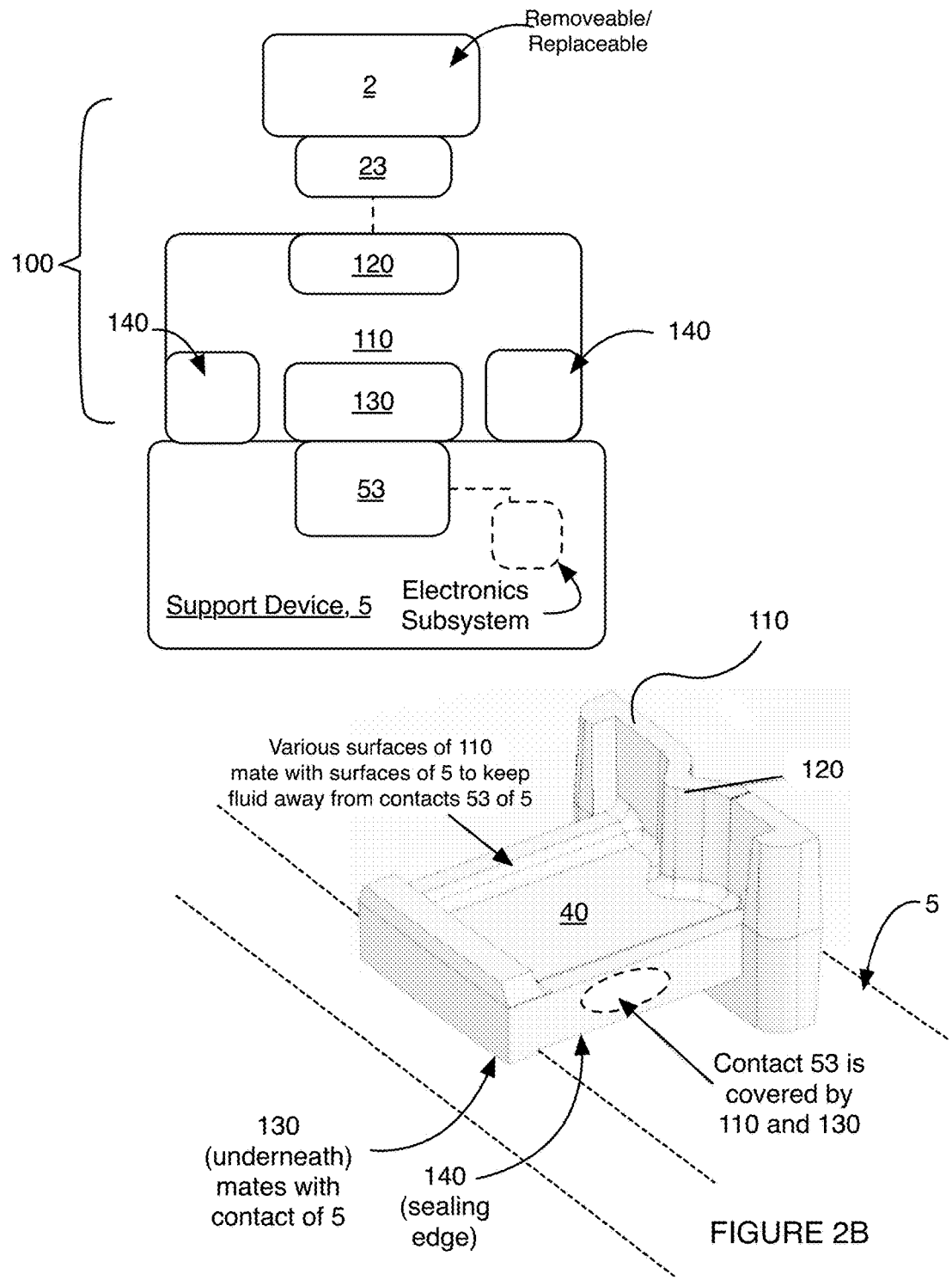

In some variations, the interface-to-electrical-subsystem coupling region 130 can extend from the body 110. Furthermore, as shown in FIGS. 2A and 4A, the interface-to-electrical-subsystem coupling region 130, 130' can also be coupled to the interface-to-transducer electrical coupling region 120, 120' in a manner that is of unitary construction with the interface-to-transducer electrical coupling region 120, 120', physically coextensive with the interface-to-transducer electrical coupling region 120, or otherwise coupled to the interface-to-transducer electrical coupling region 120 in any other suitable manner that facilitates electrical communication (e.g., a manner in which the regions are joined by a continuous path of electrically conductive material). In some variations, as shown in FIG. 2A, the interface-to-electrical-subsystem coupling region 130 can extend orthogonally from a surface of the body 110, in relation to providing electrical contact and sealing functions at corresponding positions of the transducer 2, electrode, or support device 5.

In one variation, as shown in FIGS. 2A, 2B, 3 and 5, the interface-to-electrical-subsystem coupling region 130 extending from the body 110 includes: a first broad surface 40 bounded by a first fluid sealing region 142, and a second broad surface 150 opposing the first broad surface 40 and bounded by a second fluid sealing region 152.

Figure 5:
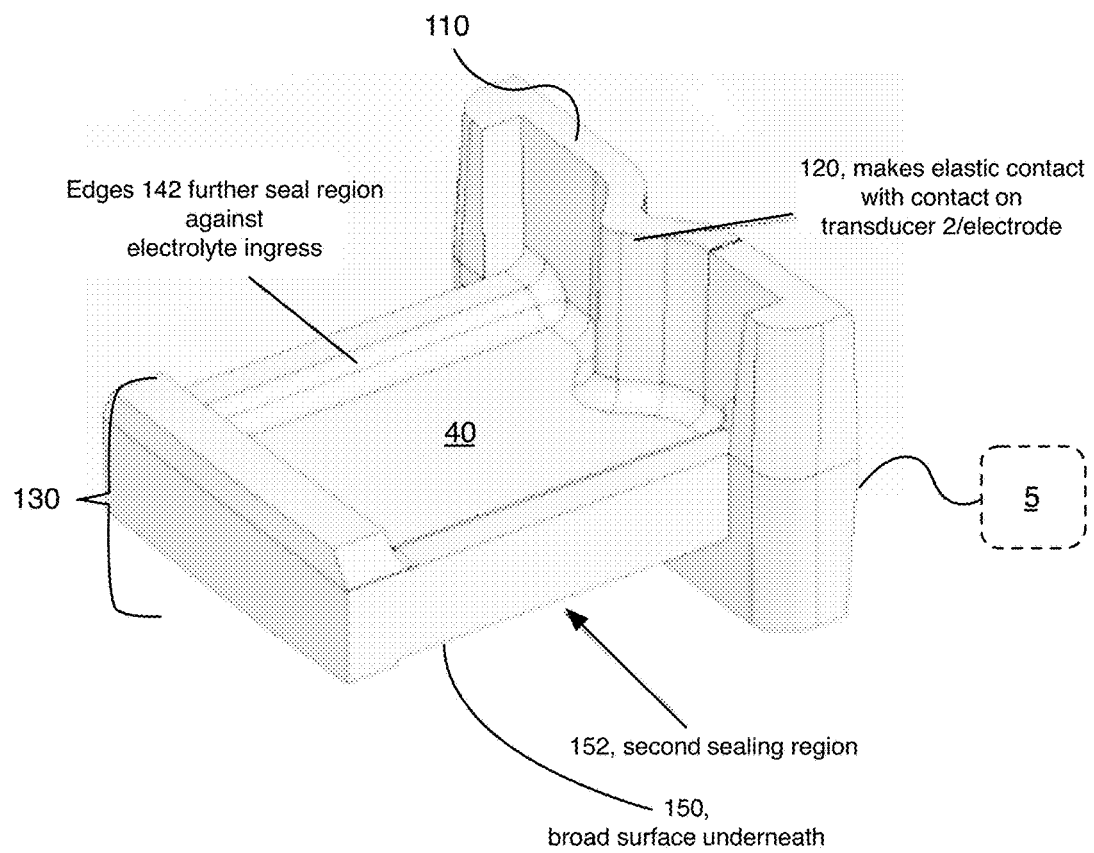
FIG. 5 depicts a schematic of an example of an embodiment of an electrical interface system.

The first broad surface 40 is configured to span a portion of the transducer 2 supporting a conductive contact that interfaces with the interface-to-transducer electrical coupling region 120 described above, wherein the first fluid sealing region 142 further seals the interface with the conductive contact and prevents ingress of fluid (e.g., electrolyte fluid) into regions surrounding the conductive contact. The first fluid sealing region 142 preferably includes a ridge of compliant material (e.g., the same material composition as the body 110, a different material composition from the body 110, etc.) peripherally surrounding edges of the first broad surface 40, in order to define an internal volume within which the conductive contact of the transducer 2 can be positioned to contact the interface-to-transducer electrical coupling region 120. In a specific example, as shown in FIG. 5, the first broad surface 40 is approximately rectangular (aside from a side of the first broad surface 40 abutting the elastically deformable coupling region), and the fluid sealing region 142 includes three peripherally situated ridges of material protruding from the three edges of the first broad surface 40 that do not abut the interface-to-transducer electrical coupling region 120.

Variations of any surfaces (e.g., broad surface 40) and fluid sealing regions can, however, be configured in any other suitable manner. For instance, the first broad surface may not be a broad surface, but a surface that otherwise complements the conductive contact or a support of the conductive contact of the transducer in any other suitable manner. Similarly, the fluid sealing region 142' can comprise any other suitable morphology of protruding material coupled to a surface of the interface-to-electrical-subsystem coupling region 130 in any other suitable manner. Alternatively, the first fluid sealing region 142' can comprise one or more of: a recessed region (e.g., a channel), an o-ring, a fluid sealant (e.g., silicone putty, hydrophobic material, etc.), and any other suitable combination of elements that provides a seal against undesired fluid (e.g., electrolyte) ingress into regions of the system 100.

Similar to the first broad surface 40', the second broad surface 150' of the variation described above is configured to span a portion of the support device associated with a conductive contact of an electronics subsystem (e.g., printed circuit board), wherein the second fluid sealing region 152' further seals the interface with the conductive contact of the electronics subsystem and prevents ingress of fluid (e.g., electrolyte fluid) into regions surrounding the conductive contact. The second fluid sealing region 152' preferably also includes a ridge of compliant material (e.g., the same material composition as the body 110, a different material composition from the body 110, etc.) peripherally surrounding edges of the second broad surface 150', in order to define an internal volume within which the conductive contact of the electronics subsystem can be positioned to form an electrical pathway with the body 110. In a specific example, as shown in FIG. 5, the second broad surface 150' is approximately rectangular (aside from a side of the second broad surface 150' abutting the body no), and the fluid sealing region 152' includes three peripherally situated ridges of material protruding from the three edges of the second broad surface 150' that do not abut the body 110.

Variations of the second broad surface 150' and the second fluid sealing region 152' can, however, be configured in any other suitable manner. For instance, the second broad surface may not be a broad surface, but a surface that otherwise complements the conductive contact or a support of the conductive contact of the electronics subsystem in any other suitable manner. Similarly, the second fluid sealing region 152' can comprise any other suitable morphology of protruding material coupled to a surface of the interface-to-electrical-subsystem coupling region 130 in any other suitable manner. Alternatively, the second fluid sealing region 152' can comprise one or more of: a recessed region (e.g., a channel), an o-ring, a fluid sealant (e.g., silicone putty, hydrophobic material, etc.), and any other suitable combination of elements that provides a seal against undesired fluid (e.g., electrolyte) ingress into regions of the system 100.

In the variations described above, the system preferably comprises an operation mode defining a sealed electrical pathway between the transducer 2 and the support device 5, wherein: the interface-to-transducer coupling region 120 is biased against an electrical contact of the transducer 2 and the first fluid sealing region 142 prevents fluid from reaching the space partially defined by the first broad surface 40 and containing the electrical contact of the transducer 2. Furthermore, in this operation mode, the interface-to-electronics-subsystem coupling region 130 is electrically coupled to an electrical contact 53 of the support device 5 and the second fluid sealing region 152' prevents fluid from reaching the space partially defined by the second broad surface 150, with the interface-to-electronics-subsystem coupling region 130 contacting the electrical contact of the support device 5.

Figure 6:
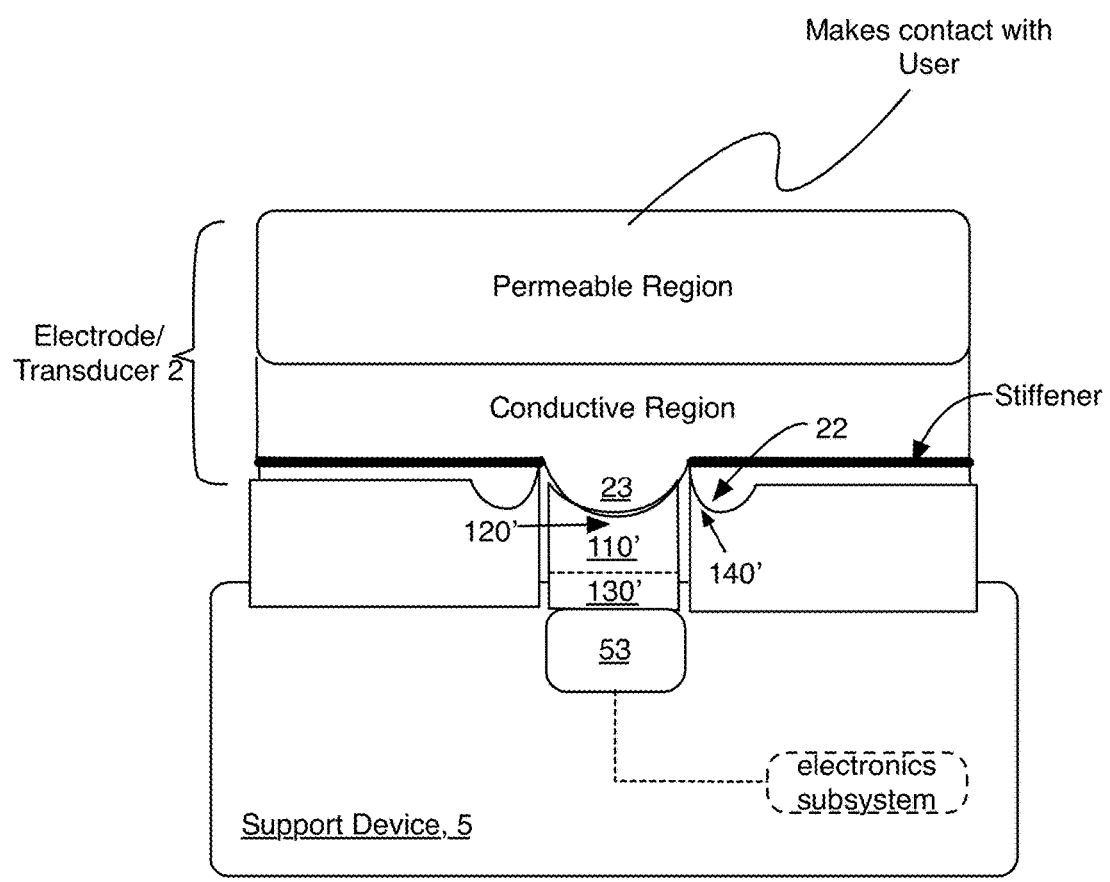
FIG. 6 depicts an operation mode of a variation of an embodiment of an electrical interface system.

In a variation of the operation mode, as shown in FIG. 6, the system 100 can define a sealed electrical pathway between the transducer 2 and the transducer support device 5, wherein: the fluid sealing region 140 defined by mating features of an interface-to-transducer electrical coupling region 120' is coupled to a complementary transducer sealing region 22, and the interface-to-transducer electrical coupling region 120' is biased against an electrical contact 23 of the transducer 2 with the fluid sealing region 140' preventing fluid from reaching the electrical contact 23 of the transducer 2.

In examples of this variation, sealing features of the transducer 2 can comprise a soft protrusion, and corresponding sealing features on the support device 5 can be hard or rigid, such that the components more likely to suffer damage are associated with a replaceable part (i.e., a replaceable transducer 2). Furthermore, any seal that is provided between the transducer 2 and the support device 5 does not have to be perfect or unusually robust (e.g., not in the manner of an implantable pulse generator header or large marine connector) in order to usefully minimize corrosion or effects of current leakage between transducer contacts. In examples of this variation, the transducer sealing region 22 may be formed of an electrically insulating material and configured to wrap partially or completely around exposed areas of the conductive region of the transducer 2, leaving only the porous region of the transducer 2 exposed, which may be desirable for controlling current flow to a body region e.g. the scalp and preventing current flow directly from the conductive region to a body region.

Variations of the operation modes can, however, be defined with system elements in any other suitable manner to form the electrical pathway from the support device 5 to the transducer 2 or electrode.

1.4 System—Example Electrodes and Support Devices Associated with the System

In examples, the system 100 can provide an electrical interface between electrodes for electrical stimulation (e.g., such as the electrodes described in U.S. application Ser. No. 14/470,683 titled "Electrode System for Electrical Stimulation" and filed on 27 Aug. 2014, U.S. application Ser. No. 14/878,647 titled "Electrode System for Electrical Stimulation" and filed on 8 Oct. 2015, and U.S. application Ser. No. 15/426,212 titled "Method and System for Improving Provision of Electrical Stimulation" and filed on 7 Feb. 2017, which are each incorporated in their entireties by this reference) and an electrode support device (e.g., such as the support devices described in U.S. application Ser. No. 15/335,240 titled "Electrode Positioning System and Method" and filed on 26 Oct. 2016, which is herein incorporated in its entirety by this reference). Additionally or alternatively, the system 100 can support or otherwise facilitate methods described in one or more of U.S. application Ser. No. 14/470,747 titled "Method and System for Providing Electrical Stimulation to a User" and filed on 27 Aug. 2014 and U.S. application Ser. No. 15/059,095 titled "Method and System for Providing Electrical Stimulation to a User" and filed on 2 Mar. 2016.

Figure 7A:
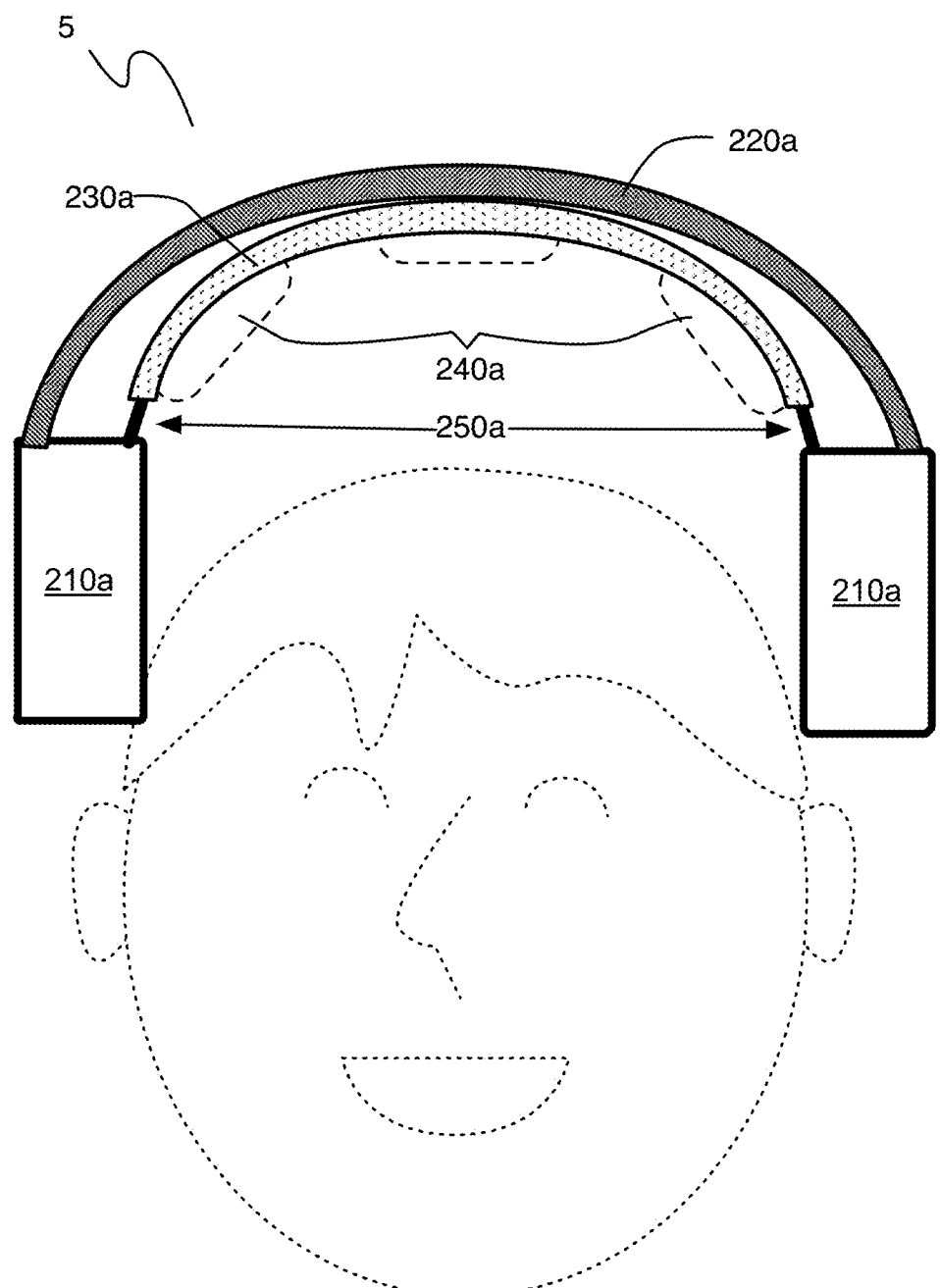
FIGS. 7A-7B depict embodiments and examples of support devices associated with an electrical interface system.
Figure 7B:
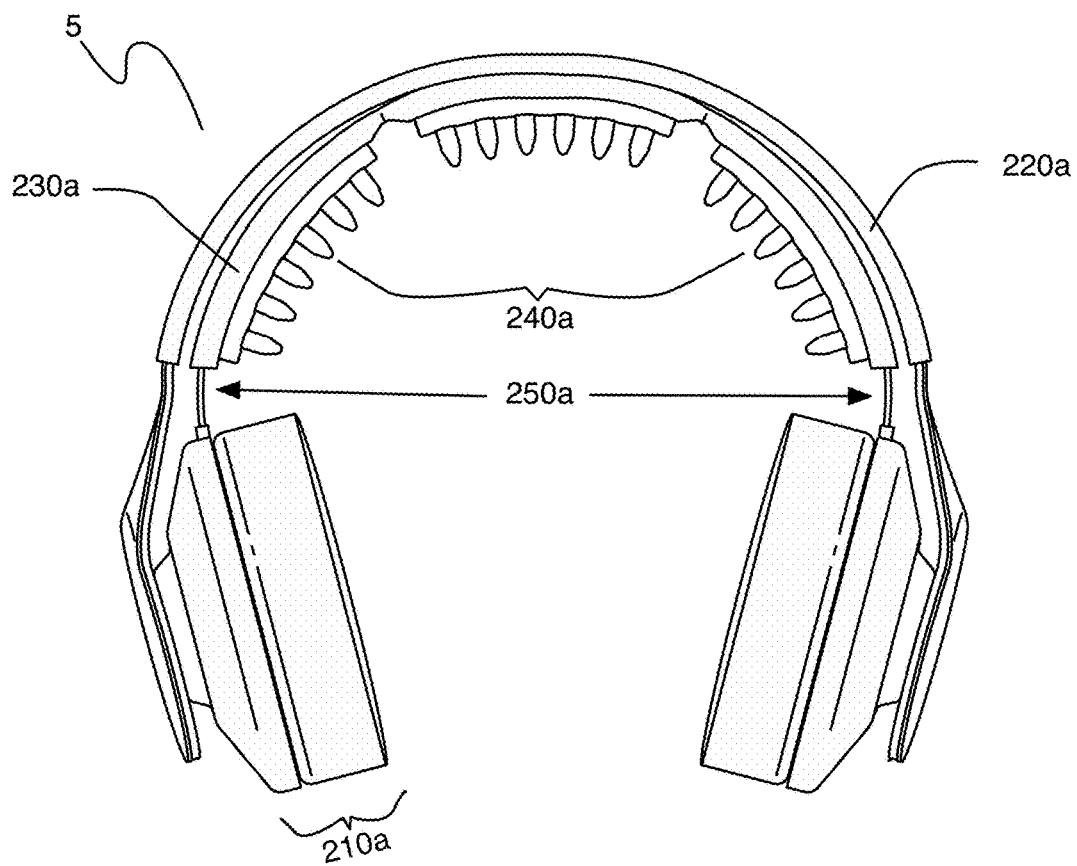
Figure 7C:
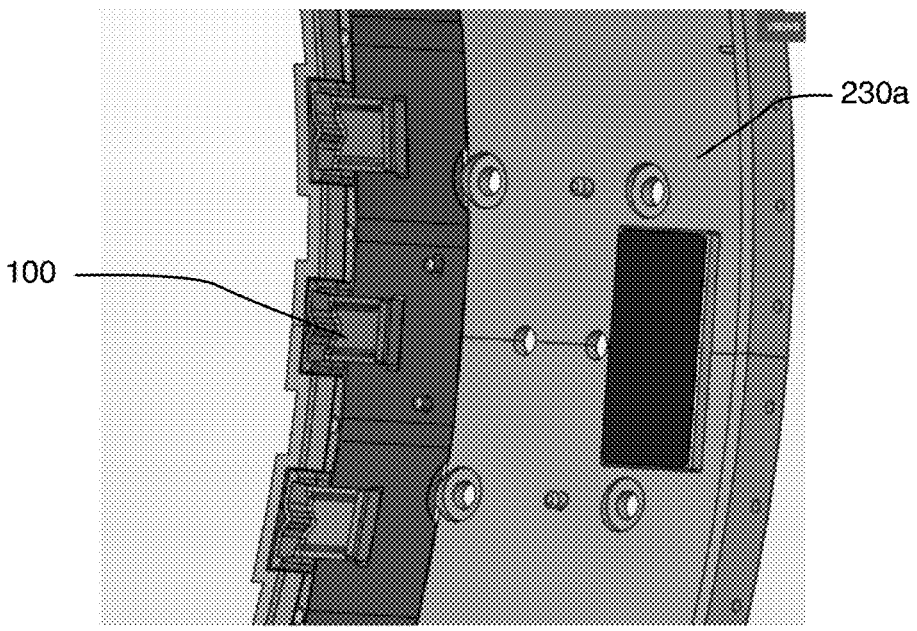
FIGS. 7C-7D depict examples of relationships between an electrical interface system and a support device.
Figure 7D:
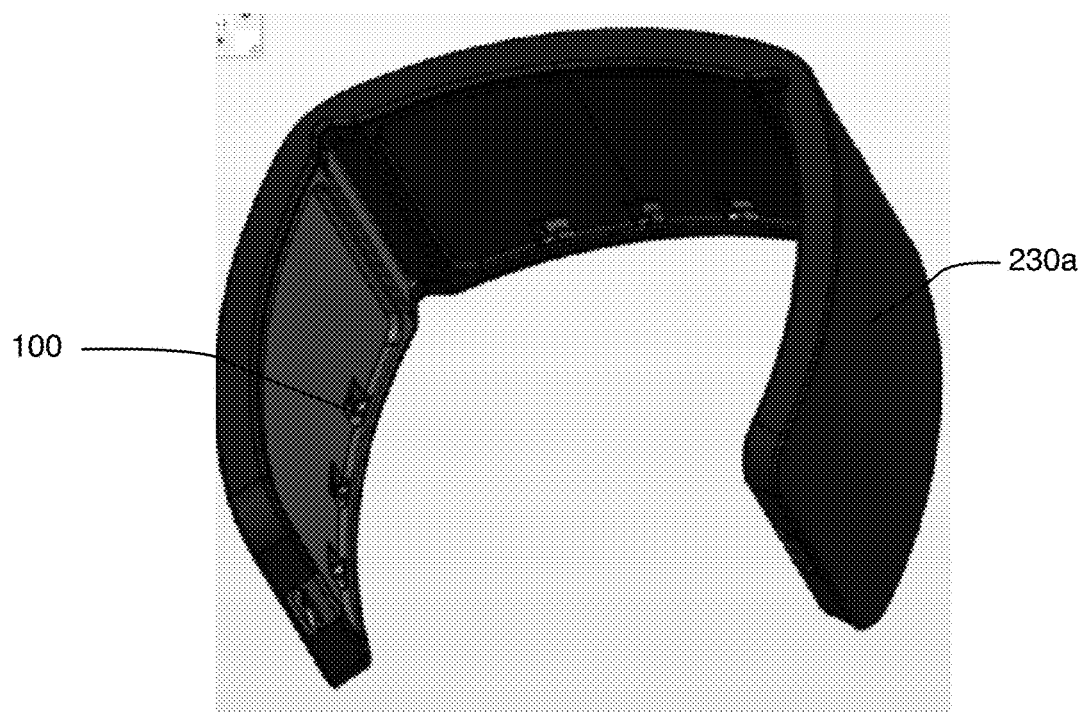
Figure 7E:
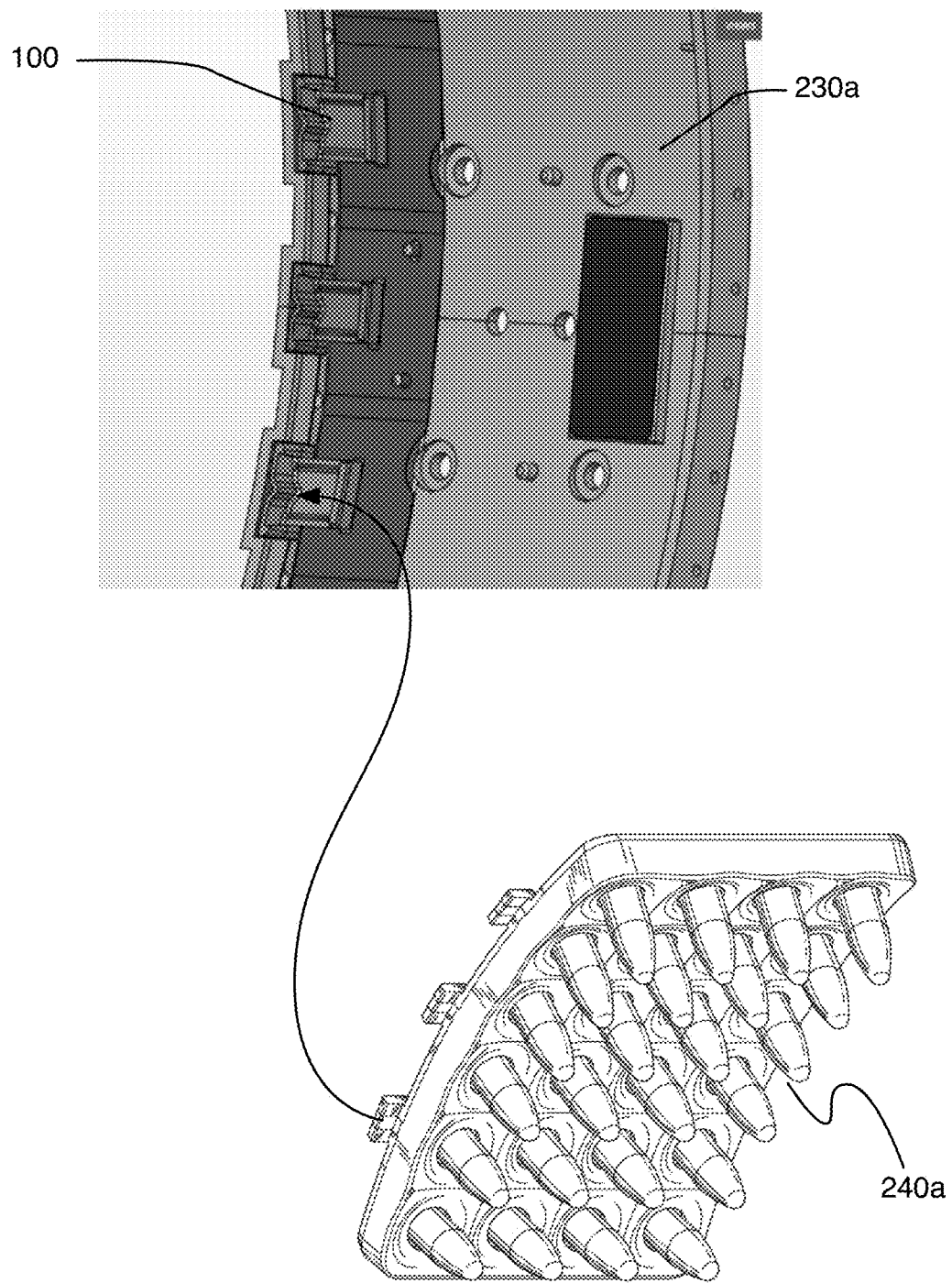
FIG. 7E depicts an example of a relationship between an electrical interface system and an electrode for stimulation of a user.

In one such example, as shown in FIGS. 7A and 7B, wherein the support device 5 comprises a set of pads 210a configured at opposing head regions of the user during use of the system; a band 220a having a first end coupled to a first pad of the set of pads and a second end coupled to a second pad of the set of pads; a bridge 230a coupled to the band and to at least one electrode 240a during use of the system; and a set of links 250a associated with the set of pads 210a, each of the set of links coupled at a first region to an interior portion of its corresponding pad, and coupled at a second region to the bridge 230a, units of the system 100 can be coupled to elements of the bridge 230a supporting the at least one electrode 240a, as shown in FIGS. 7C, 7D, and 7E. In more detail, the body 110 of the system 100 can be coupled to an internal wall of a recess of the bridge 230a configured to retain the electrode 240a, wherein the system 100 is oriented in a manner that allows the interface-to-transducer electrical coupling region 120 to make elastic contact with a metallic contact on the electrode 240a, the first broad surface 40 of the interface-to-electrical-subsystem coupling region 130 interfaces with material of the electrode (e.g., a tab) supporting the metallic contact of the electrode 240a with the first fluid sealing region 142 preventing ingress of electrolyte fluid, and the second broad surface 150 of the interface-to-electrical-subsystem coupling region 130 makes electrical contact with a contact point (e.g., metallic pad, exposed wire, or exposed electrically conductive surface) of a printed circuit board of the bridge 230a of the support device 5 with the second fluid sealing region 152 preventing fluid ingress toward the metallic pad. In a specific implementation of this example, each recess of the bridge 230a can include three units of the system, which correspond to three metallic contacts of a corresponding electrode 240a for stimulation of a head region of the user. However, variations of these examples can alternatively include any suitable number of units of the system 100 mounted to any suitable region(s) of a support device, in order to establish an electrical interface that supports removable/replaceable transducers 2 or electrodes in a manner that is robust against corrosion.

Figure 8:
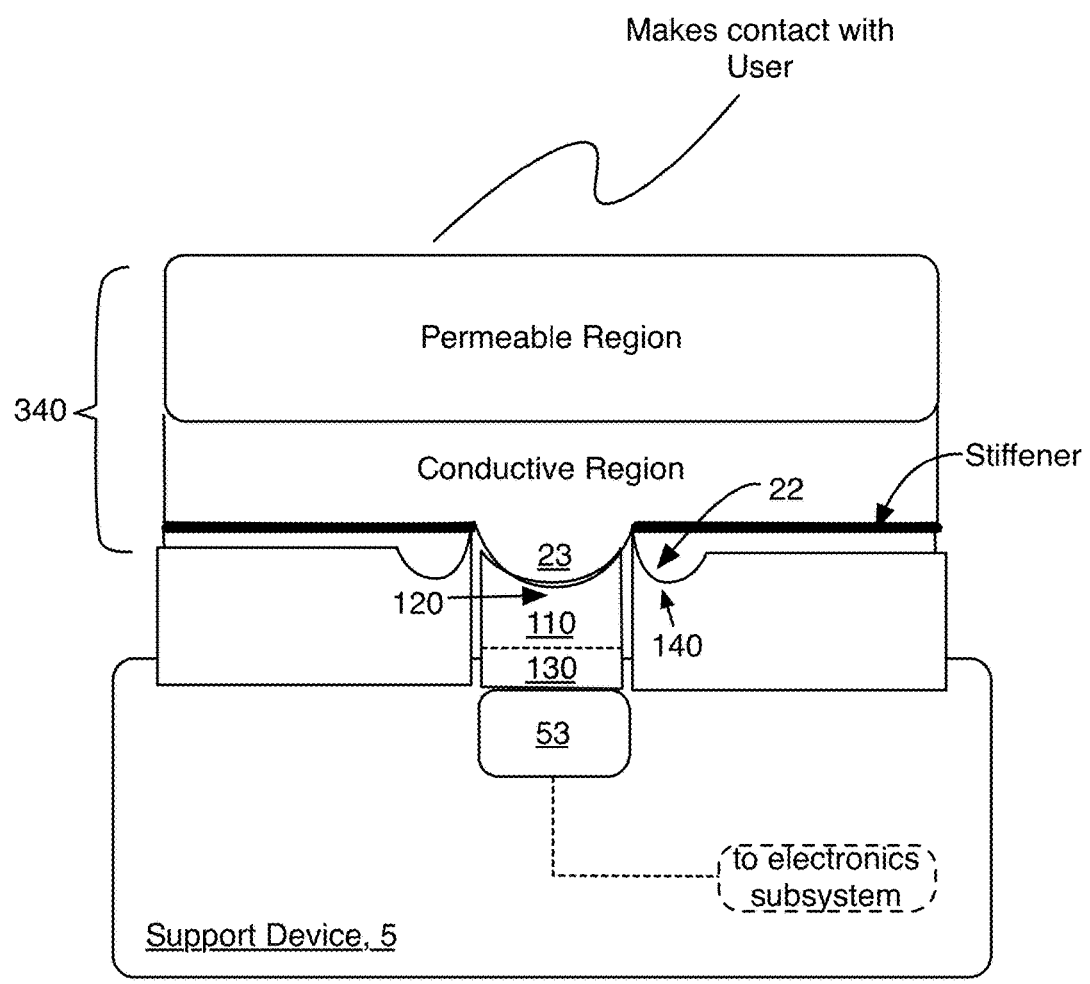
FIG. 8 depicts an operation mode of a variation of an electrical interface system, in relation to an electrode and a user.

In another variation, an example of which is shown in FIG. 8, units of the system can be mounted to a support device 5, wherein the body 110 of the system 100 is mounted to a recessed surface of the support device 5 configured to retain an electrode 340, and wherein the system 100 includes an interface-to-electrical-subsystem coupling region 130 extending orthogonally from the body 110, wherein the interface-to-electrical subsystem 130 is in communication with the support device electrical contact 53 and contiguous with the body 110 and an interface-to-transducer electrical coupling region 120. In this example, the interface-totransducer coupling region 120 comprises a concave surface surrounded by a fluid sealing region 140, wherein the fluid sealing region 140 of the system 100 comprises an annular recess defined within a bulk of elastically deformable and non-electrically conductive material circumscribing the interface-to-transducer coupling region 120. In relation to the electrode 340, a corresponding electrically conductive protrusion 23 of the electrode 340 can be configured to reversibly mate with the interface-to-transducer coupling region 120 of the system 100, wherein the protrusion 23 is circumscribed by an annular protrusion 22 of non-electrically conductive material (e.g., an annular non-conductive protrusion) that interfaces with the annular recess 140 of the system 100 (e.g., in a snap fit, in a press fit) to seal the electrical interface established by the electrically conductive protrusion 23 of the electrode 340 and the interface-to-electrical-subsystem coupling region 130 of the system 100 from fluid ingress. In this example, the electrically conductive protrusion 23 of the electrode 340 can be composed of the same material as the interface-to-electrical-subsystem coupling region 130 of the system 100, as described above; however, the electrode 340 can alternatively be composed of any other suitable materials and/or be configured in any other suitable manner. For instance, the annular protrusion 22 can be associated with the fluid sealing region of the system 100, and the annular recess 140 can be associated with the transducer 2.

Similar to the previously described examples, variations of this example can include any suitable number of units of the system 100 coupled to a support device 5 in any other suitable manner, in order to establish an electrical interface with any other suitable number of electrodes or transducers 2. Additionally, variations of this example can include embodiments where the sealing region 140 is configured to act as a mechanical attachment point (e.g., a sole mechanical attachment point or a supplementary mechanical attachment point) between electrode 340 and the support device 5. For instance, in one variation, the sealing region 140 can comprise an annular recess and the sealing feature 23 can comprise an annular protrusion which when mated together offer resistance to removal, torsion, etc. Additionally or alternatively, variations of this example may include one or more of the following embodiments: where the sealing region 140 comprises a feature such as a thumbnail recess or pull tab to aid separation of the electrode 340 and support device 5; where the sealing region 140 and/or other components of the system 100 are configured to provide flexion or limited flexion (e.g., between 1 and 20 degrees) of the joint between electrode 340 and support device 5 to aid in conforming the electrode 340 to a body part; and/or where the sealing region 140 and/or other components of the system 100 are configured to only allow connection of the electrode 340 at a particular angle of rotation with respect to support device 5 (e.g. a sealing region 140 having a keyed shape or a polygonal shape without rotational symmetry).

1.5 System—Conclusion

Examples of the system 100 can, however, comprise any other suitable element(s) or combination of elements that establish an electrical interface that supports removable/replaceable transducers 2 or electrodes in a manner that is robust against corrosion. For instance, some examples of the system 100 can implement one or more of: an o-ring, a fluid sealant (e.g., silicone putty, hydrophobic material, etc.), or any other material or morphology that prevents fluid ingress into regions of the system 100 in an undesired manner.

The system 100 and any methods associated with the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Methods associated with the system(s) described herein can support stimulation including one or more of: transcranial electrical stimulation (TES) configured to stimulate a brain region of the user in the form of at least one of: transcranial direct current stimulation (tDCS), transcranial alternating current stimulation (tACS), transcranial magnetic stimulation (TMS), transcranial random noise stimulation (tRNS), transcranial pulsatile stimulation (tPS), and/or transcranial variable frequency stimulation (tVFS, as described in one or more of: U.S. application Ser. No. 14/470,747 titled "Method and System for Providing Electrical Stimulation to a User" and filed on 27 Aug. 2014; U.S. application Ser. No. 15/426,212 titled "Method and System for Improving Provision of Electrical Stimulation" and filed on 7 Feb. 2017; and U.S. application Ser. No. 15/059,095 titled "Method and System for Providing Electrical Stimulation to a User" and filed on 2 Mar. 2016, each of which is incorporated herein in its entirety by this reference.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals or neurostimulation will recognize from the previous detailed description and from the figures and claims, modifications and changes can be made to the preferred embodiments of the invention without departing from the scope of this invention defined in the following claims.

We claim:

1. A system configured to electrically couple a transducer and a transducer support device, the system comprising:
   an electrical interface comprising:
      a body mounted to the transducer support device, the body defining an elastically deformable protrusion;
      an electrical coupling region extending from the body and contiguous with the elastically deformable protrusion, the electrical coupling region comprising:

a first broad surface, and
a second broad surface opposing the first broad surface and bounded by a fluid sealing region;
the system comprising an operation mode defining a sealed electrical pathway between the body and the transducer support device, wherein:
the elastically deformable protrusion is biased against an electrical contact of the transducer, and,
the second broad surface is electrically coupled to an electrical contact of the transducer support device and the fluid sealing region prevents fluid from reaching the electrical contact of the transducer support device.

2. The system of claim 1, wherein the elastically deformable protrusion comprises a ridge of material protruding from a first surface of the body along a height of the body, and wherein the body has a recessed region opposing the ridge of material at a second surface of the body opposing the first surface of the body.

3. The system of claim 2, wherein the electrical coupling region extends orthogonally from the first surface of the body and abuts the ridge of material.

4. The system of claim 3, wherein the first broad surface region comprises a first peripheral ridge of material coupled to superior edges of the first broad surface, and wherein the second fluid sealing region comprises a second peripheral ridge of material coupled to superior edges of the second broad surface.

5. The system of claim 1, wherein the body is mounted within a recess of the transducer support device, the transducer support device comprising a set of pads configured at opposing head regions of the user during use of the system; a band having a first end coupled to a first pad of the set of pads and a second end coupled to a second pad of the set of pads; and a bridge coupled to the band and to at least one electrode during use of the system.

6. The system of claim 1, wherein the body comprises a conductive polymer substrate.

7. The system of claim 6, wherein the conductive polymer substrate comprises carbon-bearing rubber.

8. The system of claim 6, wherein the carbon-bearing rubber comprises a volume resistivity from 1 to 100 Ohm-cm.

9. The system of claim 6, wherein the carbon-bearing rubber comprises a Shore A hardness from 20-90.

10. A system configured to electrically couple a transducer and a transducer support device, the system comprising:
an electrical interface comprising:
a body mounted to the transducer support device, wherein a base of the body comprises a first electrical coupling region;
a second electrical coupling region coupled to the body and contiguous with the first electrical coupling region, the second electrical coupling region and the body defining a fluid sealing region surrounding the second electrical coupling region;
the system comprising an operation mode defining a sealed electrical pathway between the body and the transducer support device, wherein:
the fluid sealing region is coupled to a complementary transducer sealing region, and
the first electrical coupling region is biased against an electrical contact of the transducer with the fluid sealing region preventing fluid from reaching an electrical contact of the transducer support device.

11. The system of claim 10, wherein the body is composed of a conductive polymer composition, and wherein the conductive polymer composition comprises carbon-bearing rubber.

12. The system of claim 11, wherein the carbon-bearing rubber comprises a volume resistivity from 1 to 100 Ohm-cm.

13. The system of claim 11, wherein the elastically deformable coupling region comprises a ridge of material protruding from a first surface of the body along a height of the body, and wherein the body has a recessed region opposing the ridge of material at a second surface of the body opposing the first surface of the body.

14. The system of claim 13, wherein the fluid sealing region comprises a first fluid sealing region comprising a first peripheral ridge of material coupled to superior edges of a first broad surface of the body.

15. The system of claim 10, wherein the elastically deformable coupling region extends orthogonally from the base and is physically coextensive with the electrical coupling region.

16. The system of claim 15, wherein the electrical coupling region comprises a concave surface operable to interface with an electrically conductive protrusion of the transducer.

17. The system of claim 16, wherein the fluid sealing region comprises an annular recess within a bulk of material circumscribing the electrical coupling region, the annular recess corresponding to an annular protrusion of non-conductive material circumscribing the electrically conductive protrusion of the transducer as the complementary transducer sealing region.

18. The system of claim 17, wherein the annular recess of the fluid sealing region of the system is operable to form a snap with the annular protrusion of the transducer.

19. The system of claim 10, wherein the fluid sealing region comprises at least one of an o-ring and a hydrophobic material.

20. The system of claim 10, wherein the base is mounted within a recess of the transducer support device, the transducer support device supporting a set of transcranial stimulation electrodes.

21. The system of claim 20, wherein the transducer support device comprises a set of pads configured at opposing head regions of the user during use of the system; a band having a first end coupled to a first pad of the set of pads and a second end coupled to a second pad of the set of pads; and a bridge coupled the band and to at least one electrode during use of the system.

22. The system of claim 10, further including a set of mating features including a first annular mating feature surrounding the first electrical coupling region that mates with a corresponding annular mating feature of the transducer in a press-fit operation mode, thereby producing a sealed configuration between the system and the transducer.

* * * * *

UNITED STATES PATENT AND TRADEMARK OFFICE
CERTIFICATE OF CORRECTION

| | |
|---|---|
| PATENT NO. | : 10,485,443 B2 |
| APPLICATION NO. | : 15/627717 |
| DATED | : November 26, 2019 |
| INVENTOR(S) | : Patrick Wolber et al. |

It is certified that error appears in the above-identified patent and that said Letters Patent is hereby corrected as shown below:

In the Claims

Column 15, Line 32, In Claim 5, after "system;", insert --¶--

Column 15, Line 35, In Claim 5, after "and", insert --¶--

Column 16, Line 12, In Claim 13, delete "claim 11," and insert --claim 12,-- therefor Column 16, Line 51, In Claim 21, after "system;", insert --¶--

Column 16, Line 53, In Claim 21, after "and", insert --¶--

Signed and Sealed this
Fourth Day of April, 2023

Katherine Kelly Vidal
*Director of the United States Patent and Trademark Office*